United States Patent
Magne-Drisch et al.

(10) Patent No.: US 6,448,459 B1
(45) Date of Patent: *Sep. 10, 2002

(54) PROCESS FOR THE PRODUCTION OF PARAXYLENE THAT COMPRISES AN ADSORPTION STAGE, A LIQUID PHASE ISOMERIZATION STAGE AND A GAS PHASE ISOMERIZATION STAGE WITH AN EUO-TYPE ZEOLITE

(75) Inventors: Julia Magne-Drisch, Vilette de Vienne; Fabio Alario, Neuilly sur Seine; Jean-François Joly, Lyons; Ari Minkkinen, Saint Nom la Breteche; Elisabeth Merlen, Rueil Malmaison, all of (FR)

(73) Assignee: Institut Francais du Petrole (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/556,298

(22) Filed: Apr. 24, 2000

(30) Foreign Application Priority Data

Apr. 22, 1999 (FR) .............................. 99 05153

(51) Int. Cl.⁷ .............................. C07C 5/22; C07C 7/12
(52) U.S. Cl. ........................ 585/478; 585/481; 585/482; 585/828
(58) Field of Search ................. 585/478, 481, 585/482, 828

(56) References Cited

U.S. PATENT DOCUMENTS

6,057,486 A * 5/2000 Merlen et al. ............... 585/481

FOREIGN PATENT DOCUMENTS

| EP | 0 051 318 A1 | 5/1982 |
| EP | 0 923 987 A1 | 6/1999 |
| FR | 2 768 724 | 3/1999 |

OTHER PUBLICATIONS

S.T. Sie et al., Development and Industrial Performance of a Zeolite–Based Xylene Isomerization Catalyst, Petrochemie, Nov. 1996, pp. 463–468.

* cited by examiner

*Primary Examiner*—Thuan D. Dang
(74) *Attorney, Agent, or Firm*—Millen, White, Zelano & Branigan, P.C.

(57) ABSTRACT

A process for the production of paraxilene comprises an adsorption stage (18) using toluene as a desorbent in a simulated moving bed of a feedstock previously depleted in ethylbenzene by distillation (3) or by adsortion, an isomerization stage (26) without hydrogen in liquid phase diluted with toluene from the raffinate produced, a distillation stage (27) of the raffinate that is isomerized to recover the toluene (29) that is recycled. The separated isomerate is introduced into a xylene distillation column (9). The separated ethylbenzene is isomerized separately in gas phase with hydrogen at higher temperature and is distilled (5, 2, 9) in the presence of a catalyst that comprises an EUO-structural-type zeolite, then recycled to adsorption stage (18).

17 Claims, 2 Drawing Sheets

US 6,448,459 B1

PROCESS FOR THE PRODUCTION OF PARAXYLENE THAT COMPRISES AN ADSORPTION STAGE, A LIQUID PHASE ISOMERIZATION STAGE AND A GAS PHASE ISOMERIZATION STAGE WITH AN EUO-TYPE ZEOLITE

The invention relates to a process for the production of paraxylene that combines an adsorption stage in a simulated moving bed of a feedstock with eight aromatic carbon atoms and a stage of isomerization in liquid phase of a fraction that is low in paraxylene that is recovered from said bed. It pertains particularly to the synthesis of very pure paraxylene for producing an intermediate petrochemical, terephthalic acid.

The composition of the aromatic feedstocks with eight carbon atoms varies extensively according to their origin. Generally, the content of para-and orthoxylene isomers is close to 50%, so that a single process does not make it possible to maximize the production of paraxylene. It is then necessary to combine an adsorption stage of the feedstock in a zeolitic sieve that delivers a fraction that is very high in paraxylene and a fraction that is low in paraxylene and therefore high in orthoxylene and metaxylene followed by an isomerization stage of this fraction that is low in paraxylene, as is described in the patent (G.B. 1420796). During this isomerization stage, the ratio of isomers at equilibrium is reestablished since the desirable isomers are produced at the expense of undesirable isomers.

Now, taking into account the variety of products that are introduced into the isomerization zone, the conditions of the isomerization reaction cannot be optimized. There generally follow secondary reactions of dismutation of ethylbenzene that lead to the formation of benzene and heavy aromatic hydrocarbons and dismutation of xylenes that are transformed into toluene and heavy aromatic compounds, which complicates the downstream separations and which reduces the amount of desirable isomers for the production of p-xylene and therefore the final product yield.

A prior written description in patent application FR 2 768 724, describes a combination of stages for isomerization in liquid phase of a fraction that is high in metaxylene and orthoxylene and for isomerization in vapor phase of a fraction that is high in ethylbenzene. Whereby the isomerization conditions are not adequately optimized, there also results the formation of secondary products that interfere downstream with the separation of isomers by adsorption.

In addition, a pelletized TPZ-3 catalyst that is used for the vapor phase isomerization of a feedstock that consists of ethylbenzene or a feedstock that consists of xylenes is known by patent application EP-A-51318. This application, however, ignores the incidence of secondary products in a scheme of processes that should result in the optimized production of very pure paraxylene and disregards the influence of the shaping of the catalyst.

One of the objects of the invention is to eliminate the drawbacks of the prior art and therefore to optimize the isomerization reactions of the isomers of xylenes, and thus to reduce the impurities and to increase the yield of p-xylene produced.

Another object is to combine an adsorption stage that uses in particular the toluene as a desorbent with an isomerization stage of the xylenes that use toluene as a diluent and a separated stage for isomerization of the ethylbenzene.

Another object is to isomerize separately the ethylbenzene that was previously separated with a suitable catalyst under a judiciously selected shaping.

It was noted that by combining an adsorption stage in a simulated moving bed and a catalytic isomerization stage of the collected fraction that is low in paraxylene and that contains a substantial amount of toluene and therefore in liquid phase and with no hydrogen, good results and a simplified use were observed. In addition, a substantial savings of distillation equipment was made. More specifically, the invention relates to a process for the production of paraxylene from a feedstock of aromatic hydrocarbons with eight carbon atoms that comprises orthoxylene, metaxylene, paraxylene and ethylbenzene, in which hydrocarbon feedstock (1) is enriched with ethylbenzene in an enrichment zone (2), a first fraction (3) that for the most part contains ethylenebenzene is recovered, the first fraction is isomerized in a catalytic isomerization zone (40) in vapor phase in the presence of hydrogen with a catalyst, an isomerate is recovered, the isomerate is distilled in a so-called stabilization column (5) to eliminate its light fractions, and residual isomerate (8) of the stabilization column is recycled in enrichment zone (2), whereby enrichment zone (2) delivers a second fraction (4) that is distilled in a second distillation column (9), a distillate (10) that contains the orthoxylene, metaxylene, paraxylene and a minimum quantity of ethylbenzene is recovered, said distillate (10) is recycled in at least one adsorption column, an adsorption stage in a simulated moving bed of a feedstock that comprises said distillate (10) is produced in the adsorption column that contains a zeolitic sieve, in the presence of a desorbent, a first fraction that is high in paraxylene and a second fraction that is low in paraxylene and that contains desorbent, metaxylene, orthoxylene and ethylbenzene in a quantity at most equal to 15% by weight beyond the desorbent are recovered, and one or the other of the following sequences are produced:

either said second fraction is isomerized in liquid phase in another catalytic isomerization zone (26), the isomerate is distilled in a distillation column (27), and an isomerate (30) from which desorbent has essentially been removed is recovered, or the second fraction is distilled in a distillation column (27), a fraction that contains metaxylene and an adequate quantity of desorbent are laterally drawn off (line 45), said fraction drawn-off laterally in liquid phase into another catalytic isomerization zone (26) is isomerized at least in part, the isomerized fraction is introduced (line 37) into same distillation column (27) below the lateral draw-off point of said column, optionally a portion (47a) of the fraction that is drawn off between the lateral draw-off point and the point of introduction of the isomerized fraction is recycled to carry out a washing, and an isomerate (30) from which the desorbent is removed is recovered, and isomerate (30) from which desorbent is removed is recycled in the adsorption column, the process is characterized in that the catalyst of the isomerization zone in vapor phase comprises an EUO-structural-type zeolite.

The EUO-structural-type zeolite that is contained in the catalyst, in particular the EU1 zeolite, the ZSM50 zeolite or the TPZ-3 zeolite and their process of production are described in the literature, for example patent EP-B-42226, U.S Pat. No. 4,640,829 or EP-A-51318, and are incorporated as references in patent application EP-A-923 987.

The catalyst in ball form or extrudate form can contain:

from 1 to 90%, preferably 3 to 60% by weight of at least one EUO-structural-type zeolite that comprises silicon and at least one T element that is selected from the group that is formed by aluminum, iron, gallium and boron, preferably aluminum and boron, whose Si/T atomic ratio is greater than 5, advantageously between 5 and 100, inclusive, preferably between 5 and 80, inclusive, and also preferably between 5 and 60, inclusive. Said zeolite is at least in part in acid form, i.e., in hydrogen form (H+), whereby the sodium content is such that the Na/T atomic ratio is less than 0.5, preferably less than 0.1 and even more preferably less than 0.02, from 0.01 to 2%, inclusive, and preferably from 0.05 to 1.0%, inclusive, by weight, of at least one metal of group VIII of the periodic table, preferably selected from the group that is formed by platinum and palladium and even more preferably platinum, whereby said metal of group VIII is deposited on the zeolite or on the binder, preferably selectively on the binder and that has a dispersion that is measured by, for example, chemisorption, for example by $H_2\_O_2$ titration or by, for example, chemisorption of carbon monoxide, between 50 and 100%, inclusive, preferably between 60 and 100%, inclusive, and still more preferably between 70 and 100%, inclusive. In addition, the macroscopic distribution coefficient of said metal(s), obtained from its profile that is determined by Castaing microprobe, whereby said distribution coefficient is defined as the ratio of the concentrations of said metal in the core of the grain relative to the edge of the same grain, is between 0.7 and 1.3, inclusive, preferably between 0.8 and 1.2, inclusive, optionally from 0.01 to 2%, inclusive, and preferably between 0.05 and 1.0%, inclusive, by weight, of at least one metal of the group that is formed by groups IIIA and IVA of the periodic table, preferably selected from the group that is formed by tin and indium, optionally sulfur whose content is such that the ratio of the number of sulfur atoms to the number of metal atoms of group VIII that are deposited is between 0.5 and 2, inclusive, the addition to 100% by weight of at least one binder, preferably alumina.

The catalyst may have a mechanical resistance such that the crushing value in the bed is greater than 0.7 MPa (Shell method).

The toluene can be used as a desorbent in the adsorption process in a simulated moving bed. It can thus be the diluent that is required for isomerization in liquid phase of the fraction that is obtained from the simulated moving bed that essentially contains the orthoxylene and metaxylene, and the toluene with a limited quantity of ethylbenzene.

According to a characteristic of the invention, the ethylbenzene content of the second fraction that is low in paraxylene can reach, outside of desorbent, at most 10% by weight and preferably 5 to 8% by weight.

It is possible to draw off from the distillation column that treats the isomerate or that treats the first fraction that is high in paraxylene a fraction that consists essentially of the desorbent that is recycled at least in part in the adsorption column.

The liquid phase isomerization can be carried out under the following conditions:

Temperature lower than 300° C., preferably between 200 and 260° C.,

Pressure lower than 40 bar, preferably between 20 and 30 bar,

Desorbent/isomerization feedstock ratio: less than 15%, preferably 10 to 12% by weight, Zeolitic catalyst: ZSM5, for example, Volumetric flow rate (V.V.H.) less than 10 $h^{-1}$, preferably between 2 and 4 $h^{-1}$.

By thus operating in liquid phase that is preferably diluted with toluene, at low temperature on any catalyst that can isomerize the hydrocarbons in liquid phase, the conversion into paraxylene is promoted, and the dismutation reactions of the ethylbenzene and xylenes that lead to the formation of heavy hydrocarbons are avoided.

The feedstock of aromatic hydrocarbons, low in ethylbenzene, that is introduced into the adsorption zone in a simulated moving bed can be obtained from said enrichment zone, which is a distillation of a hydrocarbon mixture or a zone for adsorption of this mixture on a specific adsorbent bed.

According to a first variant, said feedstock comprises a residue of the first distillation column, into which was introduced the mixture of ethylbenzene, metaxylene, paraxylene and orthoxylene and which is regulated such that at least 75% by weight of the ethylbenzene is recovered as distillate.

This residue can be introduced into a second distillation column, and a distillate that contains orthoxylene, metaxylene and paraxylene is drawn off that is sent into the adsorption column, and a second residue that contains heavy $C_{9+}$ hydrocarbons.

It is possible to operate the second distillation column such that it delivers said residue that contains orthoxylene and the heaviest hydrocarbons; said residue is distilled in a fourth so-called rerun distillation column (12); and a distillate that contains orthoxylene that is recycled in the isomerization zone in liquid phase is drawn off.

The distillate of the first distillation column that contains ethylbenzene is isomerized in a catalytic isomerization zone in vapor phase in the presence of hydrogen, and the second isomerate that is obtained is distilled in a so-called stabilization column to eliminate its light fractions then recycled in the first distillation column.

The conversion into paraxylene is thus maximized.

The vapor phase isomerization in the isomerization zone can be carried out under the following conditions:

Temperature higher than 300° C., preferably 350 to 480° C.,

Pressure lower than 40 bar, preferably 5 to 20 bar,

Hourly volumetric flow rate: less than 10 $h^{-1}$, preferably between 0.5 and 6 $h^{-1}$, Catalyst that contains an EUO-structural-type zeolite, $H_2$/hydrocarbon ratio that is less than 10, preferably between 3 and 6.

Since the xylenes are absent from the isomerization feedstock, the size of the isomerization unit is small, and the conversion per pass of ethylbenzene is high. Therefore, the recycling rate is lower, the overall feedstock volume is lower, and the catalyst volume is reduced.

Relative to a conventional isomerization in vapor phase of the entire fraction that is low in paraxylene that would comprise a mixture of ethylbenzene and xylenes, the hydrogen recycling will be small, whereby all of these advantages result in substantial savings.

All of the catalysts that are able to isomerize the hydrocarbons with eight carbon atoms are suitable for this invention. A catalyst that contains an EUO-structural-type zeolite and at least one metal of group VIII of the periodic table (Handbook of Chemistry and Physics, 45th Edition, 1964–1965) are preferably used in a ratio by weight that is described above. The EU-1 zeolite and the platinum are preferably used as a metal of group VIII.

According to this variant, the ethylbenzene-enriched fraction is isomerized under optimal conditions, and the quantity of hydrogen introduced is consequently adjusted, and it is immaterial that a minimum quantity of xylenes is present in the isomerization feedstock. The consumption of hydrogen is consequently reduced to the minimum. The use of a catalyst that contains an EUO-structural-type zeolite makes it possible to reduce significantly the parasitic secondary reactions of dismutation, transalkylation and cracking which result in the formation of benzene, toluene, heavy hydrocarbons and paraffins and therefore in improving the overall yield per paraxylene pass.

Furthermore, all of the isomerizations, one at low temperature and in toluene liquid phase that works on the xylenes, the other at high temperature in vapor phase that works specifically on ethylbenzene, are easier to use and more selective.

Thus, everything works toward a greater purity and a higher yield of paraxylene.

The effluent that is obtained, after having been introduced into a stabilization column to remove light gases from it, is separated by distillation into a distillate that contains benzene and into a residue that comprises heavier hydrocarbons that are also produced by dismutation, which can be recycled into the first distillation column that receives the feedstock.

According to a second variant of the process that also promotes the production of pure ethylbenzene, the adsorption feedstock in a simulated moving bed comprises a fraction that is low in ethylbenzene and that can result from a specific adsorption of a mixture of ethylbenzene, metaxylene, paraxylene and orthoxylene on a specific adsorbent in the presence of an adequate desorbent, suitable for separating said fraction from another fraction that contains at least the majority of the ethylbenzene and preferably approximately all of the ethylbenzene.

The adsorption of the mixture to recover at least the majority of the ethylbenzene can be carried out in a simulated moving bed, preferably at simulated countercurrent, in the presence of a zeolitic adsorbent that contains at least one element that is selected from the group of elements K, Rb, Cs, Ba, Ca and Sr, and optionally water. The conditions of this particular adsorption are described in, for example, U.S Pat. Nos. 5,453,560, 4,613,725, 4,108,915, 4,079,094 and 3,943,182.

The operating conditions of the first distillation column or those of the specific adsorption of the hydrocarbon mixture for recovering at least the majority of the ethylbenzene will in general be such that a fraction is recovered that contains at least 85% by weight of ethylbenzene and preferably at least 90% by weight, which will then be isomerized in vapor phase in the presence of hydrogen to maximize the production of paraxylene.

BRIEF DESCRIPTION OF THE DRAWINGS

The invention will be better understood based on the following figures that illustrate an embodiment of the process among which.

DETAILED DESCRIPTION OF THE DRAWINGS

Figure 1:
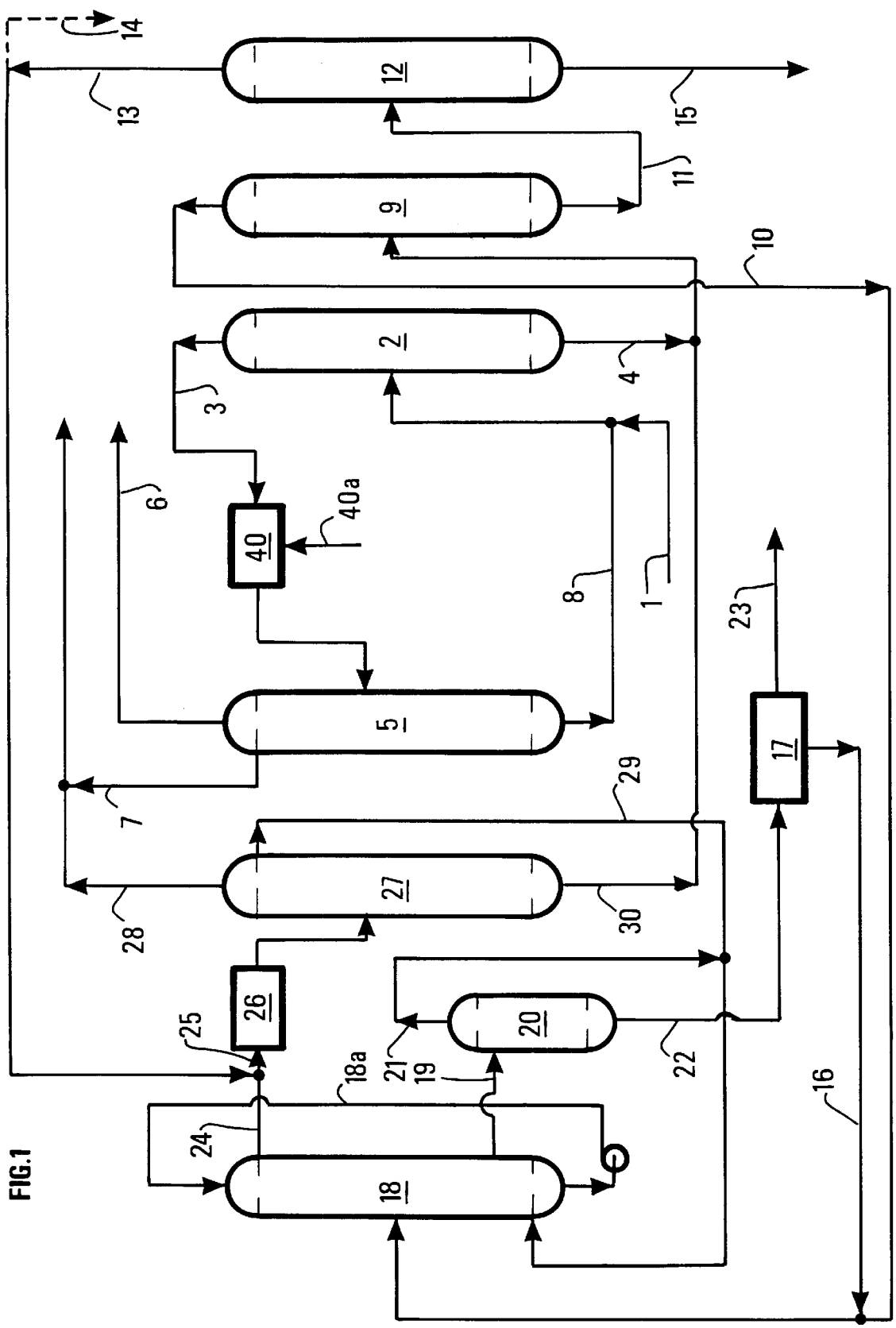
FIG. 1 shows a combination of an adsorption stage, an isomerization stage in liquid phase and a distillation stage of the isomerate that is obtained.

According to FIG. 1, an aromatic hydrocarbon feedstock 1 that contains ethylbenzene, paraxylene (P-X), metaxylene (M-X) and orthoxylene (O-X) is introduced with a stabilized isomerization effluent 8 that is described below in a distillation column 2. This column delivers a distillate via a line 3 that contains ethylbenzene and 10% by weight, for example, of paraxylenes and metaxylenes and a residue via a line 4 that contains a minor portion of ethylbenzene and xylenes (O-X, M-X, P-X). In addition, line 4 receives a line 30 that contains a distilled isomerate that is obtained from an isomerization reactor 26 that is described below. The mixture that is formed is introduced into a distillation column 9 (xylene splitter) that delivers a distillate via a line 10, that contains the metaxylene and the paraxylene and a residue via line 11 that contains orthoxylene.

The residue in line 11 is introduced into a distillation column 12 that delivers a residue via a line 15 that contains heavy hydrocarbons ($C_{9+}$) that are produced in particular by the two isomerization stages. A distillate that contains essentially orthoxylene is drawn off via a line 13 at the top of column 12 and can be recycled at the inlet of first isomerization zone 26, in liquid phase, or else recovered as a pure product via a line 14 if the distillation columns are consequently regulated.

The distillate (line 10) of column 9 is introduced at midheight, for example, of an adsorption column in a simulated moving bed 18 that contains a zeolitic sieve, Ba-X, for example. This line 10 comprises little ethylbenzene, but it does contain paraxylene that is fresh and converted in isomerization reactors and metaxylene that is fresh and not converted in these reactors.

This adsorption column is desorbed by a desorbent, the toluene that is introduced, for example, at the bottom of the column via a line 29. Between the two points of introduction of the feedstock and the desorbent, an extract is drawn off via a line 19 that contains pure paraxylene and desorbent. The latter is separated into a distillation column 20 and is recycled as distillate via a line 21 into adsorption column 18.

The paraxylene that is collected as residue via a line 22 can be recovered with an adequate purity that is close to, for example, 99.8%, or if this is not the case, purified in at least one crystallization zone 17 at high temperature, as described in the patent of the applicant (EP-B-531191 that is incorporated as a reference). The paraxylene that is recovered via a line 23 then exhibits a purity that is greater than 99.9%, for example. A mother liquid that is obtained from a centrifuging stage that is behind the crystallization stage is collected via a line 16 and recycled in feedstock line 10 to adsorption column 18, operating at simulated countercurrent. The latter further delivers a raffinate (line 24) upstream from the point of introduction of the feedstock (upstream being defined relative to the circulation of liquid current 18a that circulates from the closed loop from top to bottom in the column). This raffinate that contains toluene and metaxylene is mixed with the contents of line 13 that is high in orthoxylene and is introduced into isomerization reactor 26 via a line 25. This line advantageously contains less than 10% by weight of ethylbenzene relative to the isomerization feedstock and an amount of toluene that is greater than 10% by weight. Isomerization reactor 26 that operates with a fixed bed of a ZSM5 zeolitic catalyst, for example in liquid phase, with no hydrogen at a volumetric flow rate of 3 $h^{-1}$, at 260° C. for example, and under 30 bar, delivers an isomerization effluent that contains toluene as diluent and is high in paraxylene. This effluent is introduced into a distillation column 27 (30 plates, for example), from which are recovered a light fraction via a line 28, a toluene fraction recycled via a line 29 in the adsorption column and a residue that contains the raffinate that is isomerized via a line 30. This residue has a xylene isomer concentration that corresponds to that of the equilibrium (24/20/56% for P.X./O.X./M.X.) and an ethylbenzene content that is close to 10% by weight. It is directly sent hot in distillation column 9 to be fractionated with the residue of distillation column 2 of the ethylbenzene.

The distillate of distillation column 2 is then sent via a line 3 into catalytic isomerization reactor 40 that operates at a temperature that is close to 370–400° C. (line 40a) and in vapor phase. To save energy in the distillation costs, it is possible to tolerate up to 10%, for example, of xylenes in the distillate and the equivalent of ethylbenzene in the residue of line 4.

The ortho-, meta- and paraxylene-isomer-enriched isomerate that is obtained is stabilized in a so-called stabilization column 5 where gases that are provided by the make-up hydrogen, benzene and toluene that are formed or provided by the feedstock (line 6), light hydrocarbons (line 7 that is connected to line 28) and a column residue (line 8) are separated. The latter is mixed with the upstream feedstock of distillation column 2 of the fresh supply that contains ethylbenzene.

Figure 2:
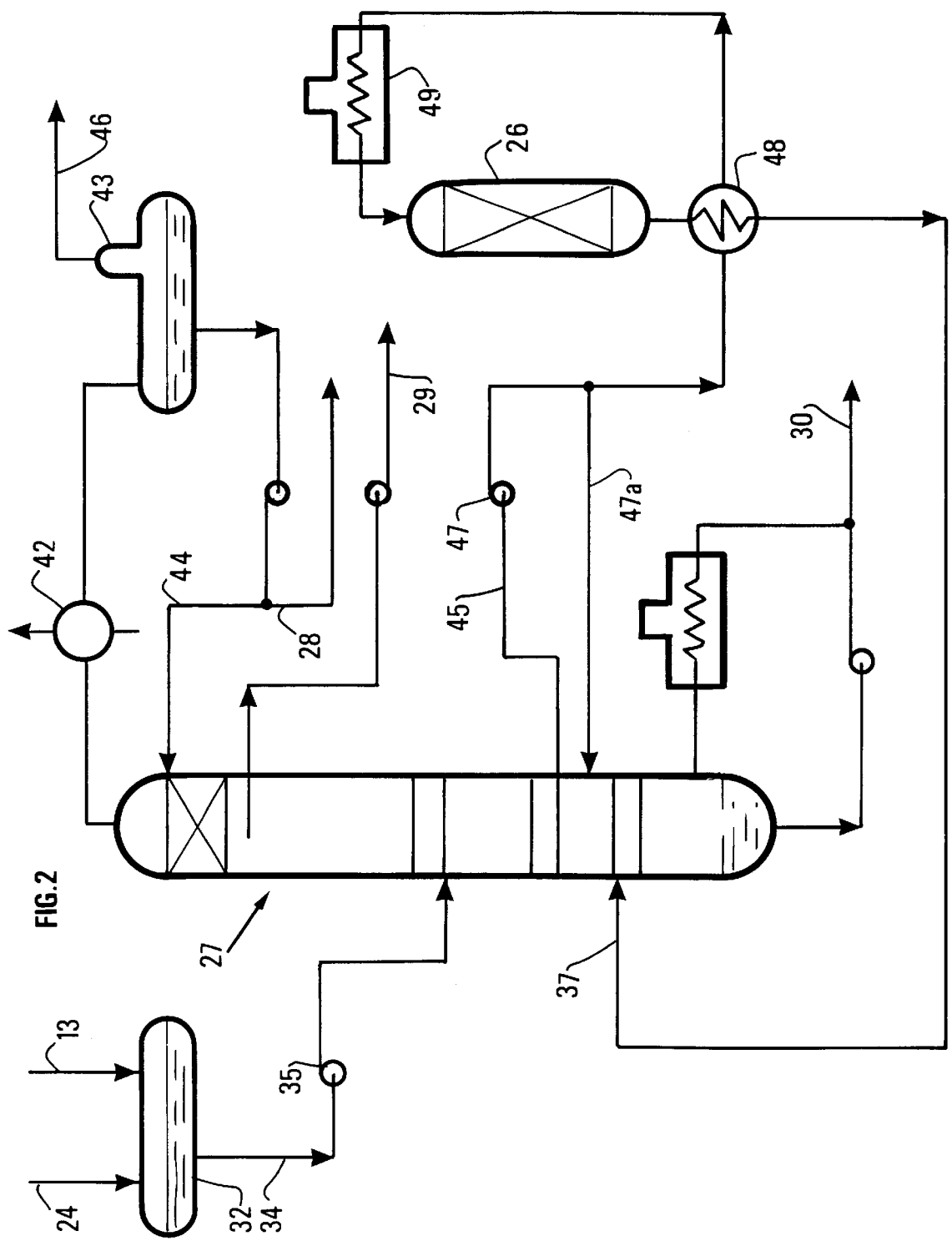
FIG. 2 represents a variant in which the distillation stage precedes the isomerization stage in liquid phase.

According to FIG. 2, the invention relates to a variant of the isomerization process that is integrated in particular for the cases where the toluene content of the raffinate that is obtained from the adsorption column, even after dilution by the recycling of orthoxylene (line 13), is greater than 20% by weight and/or when it is desired to reduce it, about 10 to 12% by weight.

The description of this FIG. 2 relies on reference figures of FIG. 1.

Thus, the raffinate (line 24) that contains toluene and that is obtained from the adsorption column is introduced into a storage tank 32 into which orthoxylene recycling line 13 that is obtained from distillation column 12 also empties. The resulting mixture (line 34) is sent via a pump 35 to the 15th plate of distillation column 27 of the toluene that contains, for example, 30 of them. The column that is operated at a top pressure of 5 bar absolute delivers a toluene current (line 29) at the 6th plate. A top distillate that comprises a reflux of the toluene and light products is at least in part condensed in a condenser 42. A large portion of the condensate is sent back to the top plate of distillation column 27 via reflux line 44 that is connected to a separation tank 43 from which the gases are evacuated at the top when there are some (line 46). A small portion of the condensate is drawn off from line 44 via a line 28 and recovers the light hydrocarbons. Recirculation of the light hydrocarbons with toluene in the adsorption column is thus avoided.

In the lower portion of distillation column 27, at the 20th plate, for example, a liquid composition that comprises 10 to 12% of toluene and orthoxylene and metaxylene, which becomes the isomerization feedstock in liquid phase at 200–260° C. is drawn off laterally via a line 45. This feedstock is pumped via a pump 47 at the reaction pressure that is required to maintain a liquid phase at the suitable temperature. In general, this pressure is less than 30 bar with this rate of toluene. A portion of this feedstock is recycled just below the draw-off plate of said feedstock as a washing fluid via a line 47a.

The isomerization feedstock is first preheated in a heat exchanger 48 via the isomerization effluent then via a preheating furnace 49 at 200° C. It is then introduced into isomerization reactor 26 that contains a ZSM-5 zeolitic catalyst bed. The reaction effluent or isomerate is cooled in heat exchanger 48 and just two or three plates are reintroduced under current draw-off plate 45 via a line 37 to be fractionated there and under the reflux plate (line 47a). An isomerization effluent from which toluene has been removed is collected as a distillation residue via line 30 that empties at the inlet of xylene distillation column 9.

The high temperature level of line 37 reduces the addition heat that is necessary for reboiling at the bottom of the column.

The following example illustrates the invention. It is carried out according to FIG. 1 but without crystallization.

The aromatic hydrocarbon feedstock has the following composition:

| | |
|---|---|
| Toluene | 5.0 |
| Ethylbenzene | 18.1 |
| P-xylene | 18.1 |
| M-xylene | 36.1 |
| O-xylene | 17.9 |
| $C_{9+}$ | 4.7 |

Separation of ethylbenzene (column 2):

| | |
|---|---|
| Column | 150–200 plates |
| Reflux rate | 55:1 to distillate |
| Top temperature | 140° C., 1.1 bar |
| Bottom temperature | 175° C.; 2.3 bar |

Content of ethylbenzene of the distillate of the column: 90% mol and 10% ethylbenzene in column residue (4).

Separation of xylenes (column 9):

| | |
|---|---|
| Column | 70 plates |
| Reflux rate | 6–7:1 to distillate |
| Top pressure | 4 bar |
| Top condensation temperature | 200° C. |
| Bottom temperature | 235° C.; 5.5 bar |

Separation of orthoxylene (column 12):

| | |
|---|---|
| Column | 30 plates |
| Top temperature | 175° C.; 2 bar |
| Reflux rate | 3.1 to the distillate |

Adsorption in a simulated moving bed at countercurrent:

| | |
|---|---|
| Sieve | Ba-X, 5.5% $H_2O$ measured by the loss due to fire (LOI) at 950° C. |
| Temperature | 170° C. |
| Number of beds | 24 |
| Pressure | 5 bar |
| Toluene/feedstock ratio | 1.6:1 |

The paraxylene that is recovered as extract exhibits a purity of 99.8% and a yield of 95%.

At the outlet of distillation column (27) of 30 plates that operate at 5 bar at the top according to FIG. 2, which recovered an orthoxylene recycling, the isomerization feedstock that is drawn off at the 20th plate has the following composition (% by weight):

|  |  |  |  |
|---|---|---|---|
| Toluene | 10.0 | Metaxylene | 60.03 |
| Ethylbenzene | 4.14 | Orthoxylene | 25.20 |
| Paraxylene | 0.18 | $C_{9+}$ | 0.45 |

Isomerization in liquid phase

|  |  |
|---|---|
| Pressure | 20 bar |
| Temperature | 260° C. |
| Zeolite | ZSM5 |
| Volumetric flow rate | 3.0 $h^{-1}$ |

The isomerization effluent has the following composition (% by weight):

|  |  |
|---|---|
| Benzene and light hydrocarbons | 0.86 |
| Toluene | 10.00 |
| Ethylbenzene | 4.14 |
| Paraxylene | 19.06 |
| Metaxylene | 46.54 |
| Orthoxylene | 17.94 |
| $C_{9+}$ | 1.46 |

This effluent is recycled in the same distillation column (27) (FIG. 2) 2 or 3 plates below the draw-off plate of isomerization feedstock (45). A portion of said draw-off is recycled just below the draw-off plate of the isomerization feedstock as reflux. The toluene is drawn off about five plates below the upper plate of the distillation column at a temperature of 190° C. The isomerate is recycled in column (9) for separation of xylenes at the 40th plate.

The distillate (line 3) of distillation column (2) of the ethylbenzene that contains about 10% impurities (paraxylene and/or metaxylene) is isomerized in the isomerization reactor in vapor phase under the following conditions:

|  |  |
|---|---|
| Temperature | 385° C. |
| Catalyst | Pt/EU-1 zeolite of the ratio Si/Al = 18/binder (alumina) (0.3%/10%/89.7%) |
| Dispersion of the metal | 95% |
| Macroscopic distribution coefficient | 0.99 |
| Value of the crushing in the catalyst bed | 1.05 MPa |
| Volumetric flow rate | 3.5 $h^{-1}$ |
| $H_2$/hydrocarbon ratio | 4:1 |
| Pressure | 9 bar |

The isomerization effluent has the following composition (% by weight):

|  |  |
|---|---|
| Benzene and light hydrocarbons | 0.75 |
| Toluene | 0.25 |
| Ethylbenzene | 21.45 |
| Paraxylene | 18.90 |
| Metaxylene | 39.04 |
| Orthoxylene | 19.06 |
| $C_{9+}$ | 0.55 |

The advantages of the process according to the invention were compared relative to those of a conventional process that comprises a distillation (xylene splitter) upstream from an adsorption in a simulated moving bed and an isomerization in the presence of hydrogen and in vapor phase of the raffinate that is obtained. It was calculated that for the same performance levels (purity and yield) and for the same investment although the device according to the invention comprises a larger number of pieces of equipment, the main advantages relate to the reduced consumption of catalyst and hydrogen utilities. For example, a reduction of at least 20% of the heating fuel consumption and about 60% of the electric power consumption in terms of pumps, compressors and air exchangers was observed. In addition, the hydrogen consumption for isomerization can represent only 20 to 30% of the amount of hydrogen that is necessary according to the conventional process.

By way of comparison, the preceding example of the invention was incorporated, except that the isomerization stage in vapor phase of the feedstock (line 3) is carried out in the presence of the same catalyst that has approximately the same dispersion of the metal and approximately the same macroscopic distribution coefficient but shaped, not extruded with a crushing value in the bed (shell) of 1.05 MPA, but pellets with a crushing value in a bed of 0.3 MPa.

The isomerization effluent produced under the same isomerization operating conditions has the following composition (% by weight).

|  |  |
|---|---|
| Benzene and light hydrocarbons | 1.85 |
| Toluene | 0.35 |
| Ethylbenzene | 22.15 |
| Paraxylene | 17.20 |
| Metaxylene | 38.70 |
| Orthoxylene | 18.00 |
| $C_{9+}$ | 1.75. |

For the entire device according to the invention, the losses per pass due to the isomerization in vapor phase in the presence of the pelletized catalyst are therefore 3.60% by weight here against 1.30% by weight with a vapor phase isomerization that comprises the EU1 catalyst in extrudate form.

Also, for the same separation capacity of column 12 that accommodates orthoxylene and the $C_{9+}$ that are formed, the residual quantity of $C_{9+}$ that remains with the orthoxylene and is recycled via line 13 at the inlet of the isomerization in liquid phase is larger. This excess $C_{9+}$ brings about a much faster deactivation of the isomerization catalyst in liquid phase (reactor 26).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/05.153, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of paraxylene from a hydrocarbon feedstock of aromatic hydrocarbons with eight carbon atoms that comprises orthoxylene, metaxylene, paraxylene and ethylbenzene, comprising: enriching the hydrocarbon feedstock with ethylbenzene in an enrichment zone, recovering a first fraction comprising at least 85% by weight ethylbenzene, isomerizing the first fraction in a catalytic vapor phase isomerization zone in the presence of hydrogen with a catalyst, recovering an isomerate, distilling the isomerate in a stabilization column to eliminate light fractions therein, recycling residual isomerate from the stabilization column to said enrichment zone, withdrawing from said enrichment zone a second fraction, distilling said second fraction in a second distillation column, recovering a distillate containing orthoxylene, metaxylene, paraxylene and a small quantity of ethylbenzene, recycling said distillate to at least one adsorption column containing a zeolite adsorbent, conducting in said adsorption column a simulated moving bed adsorption of said distillate in the presence of a desorbent so as to recover a first fraction high in paraxylene and a second fraction low in paraxylene and that contains desorbent, metaxylene, orthoxylene and a content of ethylbenzene in a quantity, based on the second fraction without the desorbent, of at most equal to 15% by weight, and conducting one of the following sequences:

either isomerizing said second fraction in liquid phase in another catalytic isomerization zone, distilling the resultant isomerate in a third distillation column, and recovering an isomerate from which desorbent has essentially been removed, or distilling the second fraction in said third distillation column, withdrawing laterally from said third distillation column a liquid phase fraction that contains metaxylene and an desorbent, isomerizing said liquid phase fraction at least in part in another catalytic isomerization zone, introducing the resultant isomerized fraction into the third distillation column below the lateral draw-off point of said column, and optionally: withdrawing a liquid fraction between the lateral draw-off point and the point of introduction of the isomerized fraction and recycling said liquid fraction in order to conduct a scrubbing step, recovering from said third distillation column an isomerate from which the desorbent is removed, and recycling said isomerate from which desorbent is removed to the adsorption column, wherein the catalyst of the vapor phase isomerization zone, in ball form or extrudate form, comprises from 1 to 90% by weight of a zeolite having an EUO structure, from 0.01 to 2% by weight of at least one metal of group VIII of the periodic table, and the addition to 100% by weight of at least one binder, whereby the dispersion of said metal in the catalyst is between 50% and 100%, the macroscopic distribution coefficient of the metal is between 0.7 and 1.3, and the catalyst exhibits a mechanical resistance such that the crushing value in the bed is greater than 0.7 MPa.

2. A process according to claim 1, characterized in that the ethylbenzene content of the second fraction low in paraxylene, based on said second fraction without the desorbent, is at most 10% by weight.

3. A process according to claim 1, wherein a fraction that consists essentially of a desorbent that is recycled at least in part to the adsorption column is drawn off from said third distillation column.

4. A process according to claim 1, wherein the isomerization in liquid phase in the isomerization zone is carried out under the following conditions:
  Temperature less than 300° C.,
  Pressure less than 40 bar,
  Desorbent/isomerization feedstock ratio: less than 15%,
  Zeolitic catalyst: ZSM5;
  Volumetric flow rate (V.V.H.) less than 10 $h^{-1}$.

5. A process according to claim 1, wherein the isomerization in gas phase in the isomerization zone in vapor phase is carried out under the following conditions:
  Temperature higher than 300° C.,
  Pressure lower than 40 bar,
  Hourly volumetric flow rate: less than 10 $h^{-1}$,
  $H_2$/hydrocarbon ratio that is less than 10.

6. A process according to claim 1, wherein the enrichment zone comprises a main distillation column into which a mixture of ethylbenzene, metaxylene, paraxylene and orthoxylene is introduced and which is regulated such that at least 75% by weight of ethylbenzene is recovered as distillate.

7. A process according to claim 1, wherein the enrichment zone is a specific adsorption zone of a mixture of ethylbenzene, metaxylene, paraxylene and orthoxylene in a specific adsorbent in the presence of an adequate desorbent, suitable for separating said feedstock into the first fraction that contains at least a large portion of ethylbenzene and of said second fraction.

8. A process according to claim 1, wherein the second distillation column is operated such that it delivers a residue that contains orthoxylene and the heaviest hydrocarbons; said residue is distilled in a fourth distillation column; and a distillate, that contains the orthoxylene that is recycled in the isomerization zone in liquid phase, is drawn off.

9. A process according to claim 1, wherein the catalyst comprises the EUO-structural zeolite and at least one metal of group VIII of the periodic table in a ratio by weight of 0.05 to 1% relative to the catalyst.

10. Process according to claim 1, wherein the catalyst contains an EU1 zeolite.

11. A process according to claim 4, wherein said temperature is between 200° C. and 260° C.

12. A process according to claim 5, wherein said temperature is between 350° C. and 480° C.

13. A process according to claim 4, wherein the vapor phase isomerization in the isomerization zone is carried out under the following conditions:
  Temperature higher than 300° C.,
  Pressure lower than 40 bar,
  Hourly volumetric flow rate: less than 10 $h^{-1}$, and
  $H_2$/hydrocarbon ratio that is less than 10.

14. A process according to claim 6, wherein at least 85% by weight of ethylbenzene is recovered as distillate.

15. A process according to claim 7, wherein said first fraction contains approximately all of the ethylbenzene.

16. A process according to claim 2, wherein the ethylbenzene content of the second fraction is 5–8% by weight.

17. A process according to claim 1, wherein the first fraction comprises at least 90% by weight ethylbenzene.

* * * * *